United States Patent [19]

Lartigau et al.

[11] 4,264,732

[45] Apr. 28, 1981

[54] ENZYMATIC COMPOSITIONS FOR ISOMERIZING GLUCOSE INTO LEVULOSE

[75] Inventors: Guy Lartigau; Albert Bouniot; Michel Guerineau, all of Melle, France

[73] Assignee: Rhone-Poulenc Industries, Paris, France

[21] Appl. No.: 926,821

[22] Filed: Jul. 21, 1978

[30] Foreign Application Priority Data

Jul. 27, 1977 [FR] France ............................. 77 23846

[51] Int. Cl.$^3$ ..................... C12P 19/24; C12N 11/12; C12N 11/04
[52] U.S. Cl. ..................................... 435/94; 435/179; 435/182; 435/813
[58] Field of Search ................. 195/31 F, 115, 63, 68, 195/DIG. 11, 65, 59; 435/94, 179, 182, 813

[56] References Cited

U.S. PATENT DOCUMENTS

| | | | |
|---|---|---|---|
| 3,733,205 | 5/1973 | Shovers et al. | 195/68 |
| 3,875,008 | 4/1975 | Yoshino et al. | 195/63 |
| 3,941,655 | 3/1976 | Heady et al. | 195/31 F |
| 3,990,943 | 11/1976 | Bouniot et al. | 195/68 |
| 4,004,980 | 1/1977 | Emery et al. | 195/68 |

OTHER PUBLICATIONS

Hamilton et al., "Glucose Isomermase: A Case Study of Enzyme-Catalyzed Process Technology" *Immobilized Enzymes in Food 2 Microbial Processes*, Plenum Press, N.Y., Olson et al. ed. (1974) pp. 85-131.

Geyer, "Glucose Isomermase: New Possibilites for the Starch-and Food Industry", *Die Starke* vol. 26, No. 7 (1974) pp. 225-232.

Lehninger, *Biochemistry*, Worth Publishers, Inc., N.Y., (1970) pp. 149, 150.

*Primary Examiner*—Thomas G. Wiseman
*Attorney, Agent, or Firm*—Burns, Doane, Swecker & Mathis

[57] ABSTRACT

The invention relates to enzymatic compositions containing intra-cellular glucose-isomerase which is enclosed in structures based on cellulose ester, their preparation and their use for isomerizing glucose into levulose.

In addition to the cellulose ester and micro-organism cells, e.g. Streptomyces phaeochromogenes, these compositions contain a sparingly water-soluble magnesium compound and optionally a sparingly water-soluble cobalt compound.

These compositions make it possible to isomerize glucose into levulose in a continuous process, with the addition of either no, or a small amount of magnesium ions to the glucose syrup to be isomerized and without the addition of cobalt ions.

16 Claims, No Drawings

ENZYMATIC COMPOSITIONS FOR ISOMERIZING GLUCOSE INTO LEVULOSE

The present invention relates to compositions based on glucose-isomerase to a process for preparing such compositions and to their use for isomerising glucose into levulose.

The use of glucose-isomerase for isomerising glucose into levulose is well known. In general, in order to obtain good results in industry and, in particular, in order to be able to operate continuously, immobilised glucose-isomerase is used. This enzyme is produced by various micro-organisms. It is possible either to extract it from a broth culture and optionally purify it, or to use directly the cells in which it is present and which have been separated from the broth, the latter method being less expensive.

Numerous methods have already been proposed for immobilising enzymes in general and glucose-isomerase in particular. This immobilisation can be carried out, for example, by adsorption on inorganic supports such as active charcoal or various alkaline earth metal carbonates or oxides. Thus, according to British Pat. Nos. 1,447,245 and 1,447,246, glucose-isomerase is adsorbed on basic magnesium carbonate. However, this process can only be applied to extra-cellular glucose-isomerase.

It has also been proposed to coat the enzymes, or the cells in which they are present, with semipermeable polymeric substances such as polyamides or cellulose derivatives, and the compositions obtained can then be made into films, fibres or particles (see British Pat. Nos. 953,414, 1,224,947 and 1,361,963).

It has also been proposed to envelop the cells containing the enzyme in polyelectrolyte flocculates (see British Pat. No. 1,368,650) and to enhance the mechanical strength of the resulting compositions by adding inorganic magnesium, calcium, iron and manganese compounds (see British Pat. No. 1,473,487).

Although these various processes make it possible to obtain compositions having a satisfactory initial enzymatic activity or good abrasion resistance, they do not improve the lifetime of the preparations in question, from the point of view of the enzymatic activity. This lifetime does not generally exceed about two weeks.

Furthermore, it is known that, in order to give good results, the glucose-isomerases which are usually used require the presence of magnesium ions and optionally a small amount of cobalt ions in the glucose syrup to be isomerised. It is therefore necessary for the levulose syrup obtained to be subjected to a deionisation treatment by means of ion exchangers, which increases the cost price of the levulose.

It has now been found according to this invention that, by enclosing micro-organism cells containing glucose-isomerase in small plates or filaments of cellulose esters, which contain, as filler, at least one sparingly water-soluble magnesium compound and optionally a sparingly water-soluble cobalt compound, it is possible to obtain compositions of intra-cellular glucose-isomerase which have an increased lifetime and require the addition of no, or only a small amount of, magnesium ions to the glucose syrup to be isomerised.

The filler in the composition of the present invention may, as indicated, contain in addition to the sparingly water-soluble magnesium compound, a sparingly water-soluble cobalt compound. This form of the composition is useful in instances where in prior art process cobalt ions would have been added to the glucose to be isomerised and would then have had to be removed from the levulose.

The term sparingly water-soluble magnesium compound is to be understood as meaning any magnesium compound having a solubility which is such that the compound liberates from 1 mg to at most 50 mg of magnesium ions per liter of water.

The term sparingly water-soluble cobalt compound is to be understood as meaning any cobalt compound having a solubility which is such that the compound liberates from 1 mg to at most 20 mg of cobalt ions per liter of water.

The micro-organisms whose cells are used in the compositions according to the invention are those which produce a glucose-isomerase having an enzymatic action which appears in the presence of magnesium ions or both magnesium ions and cobalt ions. Specific examples of such micro-organisms are *Aerobacter cloacae;* the Arthrobacters; *Bacillus coagulans; Lactobacillus brevis;* Streptomyces species such as *Streptomyces phaeochromogenes, echinatus, flavovirens, achromogenes, albus, olivaceus, olivochromogenes, violaceoniger, bikiniensis* or *venezuelae* or *Actinoplanes missouriensis.* The preferred micro-organism for carrying out the present invention is *Streptomyces phaeochromogenes.*

The cellulose ester used to form the small plates or filaments is preferably the diacetate or an industrial mixture of the diacetate and the triacetate, such as that employed for the manufacture of collodion.

The magnesium compound is preferably magnesium oxide, magnesium hydroxide, magnesium phosphate or basic magnesium carbonate or a mixture thereof, for example an industrial mixture such as magnesium hydroxycarbonate. Tribasic magnesium phosphate is the preferred filler.

The cobalt compound, where present, is preferably a cobalt II compound such as cobalt II hydroxide carbonate, orthophosphate or oxalate.

In addition to acting as an extender for the preparation, the filler performs the function of adsorbing the enzyme and providing magnesium and, optionally, cobalt ions which are required by the enzyme.

As the filler, it is also possible to use a cation exchange resin carrying sulphonic groups, which resin has been saturated with $Mg^{++}$ ions or both $Mg^{++}$ and $Co^{++}$ ions, dried, suitably in air at a temperature of about 50° C. and then ground to obtain particles suitably having a diameter of less than 0.25 mm. Such sulphonic resins are widely described in the literature (see Ion Exchange Technology, F. C. Nachod and Jack Schubert, Academic Press in New York, 1956).

Suitably enzymatic compositions of the present invention contain cells of a micro-organism containing glucose-isomerase, a cellulose ester and a filler, in the amounts defined below.

The amount of cellulose ester employed in the said compositions is suitably from 25 to 100%, preferably about 50%, by weight of dry product, based on the weight of the dry micro-organism cells.

The filler is suitably from 5 to 100%, preferably about 50% by weight of dry material based on the weight of the dry cells. The amount of the magnesium compound in the filler is suitably from 50 to 100% by weight of the filler and the amount of cobalt compound is correspondingly from 50 to 0% by weight of the filler.

The maximum proportions of the filler and cellulose ester can be increased beyond the limits indicated above, but obviously at the expense of the enzymatic activity of the composite material obtained. Furthermore, the use of too little ester tends to lead to a product having poor cohesion.

The proportion of micro-organism cells, cellulose ester and filler employed in the particularly preferred enzymatic compositions of the invention are defined below. The proportions by weight of the various constituents of the enzymatic compositions refer to the dry material:

from 40 to 60% by weight of micro-organism cells,
from 20 to 30% by weight of cellulose ester, and
from 20 to 30% by weight of filler, containing
from 15 to 20% by weight of a magnesium compound and from 5 to 10% by weight of a cobalt compound based on the total composition.

An enzymatic composition according to the invention can advantageously be prepared in the manner described below.

After having preferably subjected the cells to a heat treatment, which results, inter alia, in sterilisation of the cellular mass and destruction of certain undesirable enzymes (such as proteases) which are less resistant to heat than glucose-isomerase, the cells are separated by centrifugation from the substrate in which they have developed. The slurry obtained is then dried until it has a dry material content of 20 to 95%, preferably about 30%, by weight.

The resulting slurry is intimately mixed with a filler comprising a sparingly soluble magnesium compound and optionally a sparingly soluble cobalt compound, the proportion of this total filler being from 5 to 100%, preferably about 50%, by weight of the total weight of the cells.

The cellulose ester (e.g. the abovementioned industrial mixture of the diacetate and the triacetate) is then added to the resulting mixture in an amount of 25 to 100%, preferably about 50%, of the weight of dry cells and in the form of a 5 to 20% w/v, preferably about 10% w/v, sol in a water-miscible organic solvent which is preferably acetone. If desired, the cellulose ester may be added before the filler.

A water/solvent mixture similar to that used to form the cellulose ester sol is then added to the resulting slurry which contains the cellulose ester, in order to give the final mixture the appropriate consistency for producing the shape which it is proposed to employ. The amount of solvent to be added can be from 1 to 10 times the weight of the dry cells employed.

The amount of water which has been mixed with the solvent beforehand is such that, allowing for the moisture in the cells, the water contained in the final mixture represents 0.6 to 8 times, preferably about 3 times the weight of cellulose ester employed; furthermore, the final weight ratio of water/solvent should be less than 0.2:1.

These limits to the relative proportions of water solvent and cellulose ester determine the properties of the final product; thus, with too little water, the porosity of the structure obtained is low and the exchange capacities will therefore be poor; with too much water or insufficient solvent, the final product lacks cohesion or has poor enzyme retention.

The order in which the constituents are added is not necessarily that which has now been indicated above, but can be altered to suit the manufacturing process.

Frequently, where the method of preparation of the cells containing the enzyme gives rise to cell walls which allow strong diffusion of the enzyme (depending on the conditions under which the micro-organisms are cultured, heat-treated or separated), it is preferable to subject the cells to a mild treatment with glutaraldehyde. This treatment can be carried out either at the end of the culture, or on the cell slurry, preferably with the cellulose ester but before introducing the filler (it then being necessary for the latter to be introduced last), or again, as will be seen below, after the mixture has been shaped. In the case where the glutaraldehyde treatment is carried out on the cells or on the slurry of cells and ester, 0.5 to 6%, preferably about 3%, of glutaraldehyde based on the weight of dry cells, is normally used. The mixture with glutaraldehyde is preferably intimate and it is preferably left to react for 10 minutes to 1 hour at 10° to 30° C.

Finally, the fluid paste obtained, which may have been homogenised e.g. by means of a propeller stirrer or a turbine stirrer, contains the cells, the filler, the cellulose ester, water, the solvent and optionally glutaraldehyde.

This paste can then be spread as a thin layer (1 to 3 mm thick) on a substrate and left to dry, for example, in air at a temperature of 15° to 30° C. After about one hour, when it is not yet brittle, it can be cut up into small units (plates) having a side length of a few millimeters e.g. 1 to 10 mm. After detaching the plates from the substrate, drying is continued without allowing the brittle phase to be reached.

If desired, it is at this stage of the preparation that the glutaraldehyde treatment can be carried out by dipping the dried plates in an aqueous solution of glutaraldehyde.

The product obtained can then be used for isomerising glucose solutions.

The manufacture of small plates, described above, represents a preferred embodiment of the invention. However, it is possible to shape the paste by any other known means, in particular by extrusion if it is desired to produce filaments instead of small plates. Before optionally drying the filaments in depth, their surface is coagulated immediately after extrusion, either by a stream of hot air or by immersion in water for a few minutes. The small plates and filaments can be kept either in the dry state or in suspension in a liquid which is preferably water to which a suitable antiseptic (e.g. formaldehyde) has been added.

The small plates and filaments according to the invention exhibit numerous advantages, in particular, their ability to be used for a continuous process in a column.

Their mechanical strength is very good, even after they have been used for a very long time. The pressure loss on passing the solution to be isomerised through the column is very low and stable with time.

These preparations have a very long lifetime; the activity half-life, or the time after which the activity of the preparation has been reduced by half, usually easily exceeds 1,000 hours. Furthermore, the decrease in activity takes place very gradually and uniformly.

The mean rate of production of levulose per unit weight is good.

It is not necessary to add magnesium ions and cobalt ions, in the form of soluble salts, to the solutions to be isomerised, since the magnesium and optionally cobalt (where needed) in the filler are sufficient to activate the enzyme. However, in certain cases, it is possible to add up to 10 mg of magnesium ions per liter of solution to the solutions to be isomerised. In any case, the amount of magnesium ions in the levulose syrup obtained should normally not exceed 10 mg/liter, which is entirely acceptable from the nutritional point of view. As regards the cobalt content, this should normally not exceed 1 mg/liter. The fact that the levulose syrup contains these very low contents of magnesium and optionally cobalt ions means that long and expensive purification operations are not required, since the isomerised syrup is substantially free from impurities.

The compositions according to the invention, are suitably employed in the manner described below for isomerising glucose.

The composition which is in the form of small plates or very short filaments, is placed in a vertical cylinder, e.g. made of glass, which is surrounded by a jacket in which a stream of water circulates, making it possible to maintain a temperature of 50° to 75° C., preferably about 60° C. This cylinder is fed, preferably through the top, with an aqueous glucose solution having a concentration which does not exceed 60% by weight and is preferably about 45%, the enzymatic preparation being immersed in the liquid. The pH of this feed solution is adjusted before hand to 8 to 9, preferably to about 8.5, e.g. with sodium hydroxide. The feed rate is advantageously set so as to maintain a constant degree of conversion of the glucose throughout the operation. In order for the operation to have a good profitability, this degree of conversion is generally of the order of 40 to 50%, preferably about 42%. It is therefore necessary gradually to reduce the feed rate as the activity of the preparation decreases.

As mentioned above, it is unnecessary to add cobalt ions to the feed solution of glucose and it is not normally necessary to add magnesium ions thereto, but an addition ranging up to 10 mg per liter of solution may be considered desirable. The solution leaving the cylinder generally contains 2 to 10 mg/liter of magnesium ions and the content of cobalt ions should preferably never exceed 1 mg/liter.

It is also unnecessary to readjust the pH during the operation. The pH of the solution leaving the cylinder is suitably of the order of 7.5.

No abnormal coloration is found to appear in the isomerised solutions leaving the cylinder, except during the first few hours of operation. In order to overcome this, it is possible, during these first few hours, to increase the feed rate of the glucose solution so as to wash the column. In normal operation, the increase in the coloration of the solution between the inlet and the outlet of the reactor remains below 20 APHA. (ASTM STANDARD SPECIFICATION D 1209-54).

In the Examples which follow and serve to illustrate the invention, the levulose formed is determined by a colorimetric method with anthrone, using solutions of known strength as the reference. [See HALHOOL and KLEINBERG, Analytical Biochemistry, 50, pages 337-343 (1972).]

The enzymatic activities, expressed in U/g, are the number of micromols of levulose formed in 1 minute at pH 7.5 and at 60° C.

EXAMPLE 1

A slurry is used which contains 16% of dry material and originates from the centrifugation of a culture for producing Streptomyces phaeochromogenes. The activity of the cells is 150 U per gram of dry material. This slurry is placed in a ventilated oven at 35° to 40° C. and left until a paste containing 30% of dry material is obtained. This paste (52 g) is mixed with magnesium hydroxy-carbonate (1.1 g) as filler. An acetone solution (69 cc.) containing 100 g of cellulose per liter is added to the mixture. Acetone (60 cc.) is added and the whole is homogenised by means of a propeller stirrer (11,000 revolutions/minute) for a few minutes. The slurry is spread onto glass plates as a 2 to 3 mm thick layer, using an apparatus for preparing thin layer chromatography plates. The plates are left to dry in air for 2 hours and the preparation is then cut up into small plates having a side length of 3 to 5 mm. These small plates are detached and drying is allowed to proceed up to a dry material content of 80 to 90% by weight. The following enzymatic composition is obtained (the % being expressed as weight of dry material):

66% of micro-organism cells,
4.7% of magnesium hydroxy-carbonate, and
29.3% of cellulose acetate.

Measurement of the activity of these small plates gives 52 U/g, which corresponds to a fixing efficiency of about 50%.

The resulting enzymatic composition (25 g) is introduced into a vertical glass cylinder, which has a diameter of 25 mm and is equipped with a double jacket in which water circulates at 60° to 61° C. The cylinder containing the enzymatic composition is fed with a glucose solution (450 g/liter), the enzymatic composition being immersed in the solution. The pH of the glucose solution is adjusted to 8.5 to 8.7 with sodium hydroxide. The feed rate is set so as to maintain a constant degree of conversion of 42%. It is therefore necessary gradually to reduce the feed rate during the operation. Initially, this feed rate is 65 cc/hour. It has decreased by half after 900 hours and is reduced to a quarter after 2,200 hours.

If the operation is stopped at this moment, the mean production of levulose is evaluated at 480 kg per kg of the enzymatic composition employed.

The magnesium ion content in the solution leaving the cylinder varies between 10 and 2 mg/liter during the operation.

The pH of the solution leaving the cylinder is about 7.5.

The mechanical strength of the composition has not altered and the pressure loss has remained less than 1 cm of water per meter.

EXAMPLE 2

An enzymatic composition is prepared as described in Example 1, except that the filler magnesium hydroxy-carbonate is replaced by tribasic magnesium phosphate $[Mg_3(PO_4)_2.8H_2O]$ (2.2 g) and the cells used have an enzymatic activity per unit weight of dry material which is twice that of the cells of Example 1. The enzymatic composition obtained is as follows (the % being expressed as weight of dry material):

63% of micro-organism cells,
9% of tribasic magnesium phosphate, and
28% of cellulose acetate.

The composition is used to convert glucose to levulose as described in Example 1. The initial feed rate is 65 cc/hour. It has decreased by half after 1,300 hours and is reduced to a quarter after 1,700 hours. The magnesium ion content in the solution leaving the cylinder is of the same order as in Example 1.

EXAMPLE 3

An enzymatic composition is prepared as described in Example 1, except that magnesium hydroxycarbonate (1.1 g) and cobalt II carbonate ($CoCO_3$) (1.1 g) are used as the filler. The following enzymatic composition is obtained (the % being expressed as weight of dry material):

63% of micro-organism cells,
4.5% of magnesium hydroxy-carbonate,
4.5% of cobalt II carbonate, and
28% of cellulose acetate.

The composition is used to convert glucose to levulose as described in Example 1. The initial feed rate is 75 cc/hour. It has decreased by half after 1,000 hours and is reduced to a quarter after 2,250 hours.

The magnesium ion content in the solution leaving the cylinder varies between 9 and 2 mg/liter during the operation. The cobalt ion content remains less than 0.9 mg/liter.

EXPERIMENT A

By way of comparison, small plates are prepared as described in Example 1 from the same slurry but without adding any filler.

Finished small plates are introduced into a tubular reactor. The small plates pack badly because they tend to float in the sugar solution. The feed solution does not contain any magnesium. In order to ensure a pH of 7.5 at the outlet, the pH of the feed solution must be adjusted to 9 to 9.3. Consequently, the solution leaving the reactor is slightly coloured. In order to obtain a degree of conversion of 42%, the initial feed rate must be limited to 30 cc/hour for a glucose solution containing 450 g/liter. After 100 hours of operation, the feed rate is less than 15 cc/hour.

EXAMPLE 4

An enzymatic composition is prepared as described in Example 1, except that the filler magnesium hydroxycarbonate is replaced by tribasic magnesium phosphate [$Mg_3(PO_4)_2.8H_2$)] (2.2 g) and cobalt II carbonate ($CoCO_3$) (1.1 g) and the cells used have an enzymatic activity per unit weight of dry material which is twice that of the cells of Example 1.

The enzymatic composition obtained is as follows (the % being expressed as weight of dry material):

60.5% of micro-organism cells,
8.5% of tribasic magnesium phosphate,
4.2% of cobalt II carbonate, and
26.8% of cellulose acetate.

The composition is used to convert glucose to levulose as described in Example 1. The initial feed rate is 65 cc/hour. It has decreased by half after 1,500 hours and is reduced to a quarter after 1,900 hours.

The magnesium and cobalt contents in the solution leaving the cylinder are of the same order as in Example 3.

EXAMPLE 5

Small plates of enzymatic composition (25 g), which have been prepared as described in Example 3, are dipped in a volume of water which is sufficient to immerse the small plates and contains glutaraldehyde (0.5 g). The reagents are left in contact for 30 minutes at 20° C.

The small plates are then drained and the composition treated in this way is used for isomerising glucose under the same conditions as in Example 1. The initial feed rate is 45 cc/hour. It has decreased by half after 1,500 hours.

The contents of magnesium ions and cobalt ions in the solution leaving the cylinder are of the same order as in Example 3.

EXAMPLE 6

Glutaraldehyde is added at the rate of 6 g per 100 g of dry material to the culture for producing Streptomyces phaeochromogenes when production has ended. The reagents are left in contact for 1 hour at pH 7.5 and at 25° C.

The cells are centrifuged and then treated as described in Example 1. The initial feed rate is 77 cc/hour. It has decreased by half after 1,100 hours and is reduced to a quarter after 1,600 hours.

The contents of magnesium ions and cobalt ions in the solution leaving the cylinder are of the same order as in the preceding Examples.

EXPERIMENT B

An enzymatic composition is prepared in the manner described in Example 1, but without adding any filler and with the introduction of glutaraldehyde (0.5 g) (in the form of a commercially available 25% strength aqueous solution) at the same time as the cellulose acetate solution is mixed with the cell slurry. The composition obtained (25 g) is used, in the same cylinder as that of Example 1, to isomerise a glucose solution (450 g/liter), to which [$MgSO_4.7H_2O$] (1.23 g/liter) has been added. A certain difficulty is experienced in filling the tube and ensuring the good circulation of the solution, because the small plates tend to float.

The initial feed rate is 48 cc/hour. It has decreased by half after 1,500 hours and is reduced to a quarter after 2,300 hours.

The levulose production is evaluated at 560 kg per kg of composition. However, the magnesium ion content of the solution leaving the cylinder is 100 mg/liter, which necessitates purification of this solution by means of ion exchangers.

EXAMPLE 7

By following the procedure described in Example 1, a cell slurry containing 30% of dry material is prepared, the activity of which is 250 U/g. This slurry (100 g) is mixed with [$Mg_3(PO_4)_2.8H_2O$] (13 g), a cellulose acetate solution (125 cc) containing 100 g/liter, and acetone (60 cc). The slurry obtained is homogenised and introduced into the barrel of a syringe (grease gun) which has an orifice of 2 mm diameter. The twisted strand obtained by extrusion therefrom is collected in a receiver containing water (2 liters) at 25° C. The extrudates are left in the water for 2 minutes and then drained and dried in a ventilated oven at 35° C. When they have become brittle, which occurs at a solids content of 85 to 90% by weight, they are roughly broken up to obtain 3 to 8 mm long rods having the following composition (the % being expressed as weight of dry material):

54% of micro-organism cells,
23.5% of basic magnesium triphosphate, and
22.5% of cellulose acetate.

An activity test shows that they possess an activity of 85 U/g, which corresponds to a fixing efficiency of 70%.

These rods (25 g) are introduced into a tube for endurance testing, and an initial feed rate of 120 cc/hour of a solution containing 450 g of glucose per liter and no magnesium makes it possible to obtain a degree of conversion into levulose of 42%. The feed rate is still 60 cc/hour after 600 hours of operation.

Finally, it is found that the overall production is 525 kg of levulose per kg of rods employed, at the mean rate of 15 kg per day.

EXAMPLE 8

An enzymatic composition is prepared as described in Example 7, except that $[Mg_3(PO_4)_2.8H_2O]$ (10 g) and cobalt carbonate $(CoCO_3)$ (3 g) are used as the filler. The extrudates obtained, which have a dry material content of 85 to 90% by weight are broken up to obtain 1 to 8 mm long rods having the following composition (the % being expressed as weight of dry material):

54% of micro-organism cells,
18.1% of tribasic magnesium phosphate,
5.4% of cobalt carbonate, and
22.5% of cellulose acetate.

An activity test shows that they possess an activity of 100 U/g, which corresponds to a fixing efficiency of 90%.

These extrudates (25g) are introduced into a tube for endurance testing and this tube is fed with 120 cc/hour of a solution containing 450 g of glucose per liter, no cobalt ions are 10 mg/kg of a solution of magnesium ions in the form of the phosphate; the degree of conversion is 42%. After 950 hours of operation, the degree of conversion is still 42% for a feed rate of 60 cc/hour. The overall production is then 865 kg of levulose per kg of rods employed, at the mean rate of 14 kg/day, if the production is stopped when the feed rate has reached 25% of its initial value, keeping the degree of conversion at 42%.

Determination of the metal ions in the effluent syrup indicates a magnesium ion content of 10 mg/liter of isomerised solution and a cobalt ion content of 0.8 mg/liter of isomerised solution.

EXAMPLE 9

The same enzymatic composition as described in Example 8 is prepared, but the cobalt compound is not added.

A glucose solution is isomerised using extrudates (25 g) and operating under the conditions described in Example 8. The initial feed rate is 115 cc/hour.

After 600 hours of operation, the degree of conversion is 42% for a feed rate of 58 cc/hour.

The feed rate reaches 25% of its initial value after 1,300 hours, keeping the degree of conversion at 42%.

The overall production is 620 kg of levulose per kg of rods employed, at the mean rate of 9 kg/day.

We claim:

1. An enzymatic composition for isomerising glycose to levulose, which composition is in the form of small plates or filaments which comprise cells of a micro-organism containing glucose-isomerase immobilized therein in an amount which, in the presence of magnesium ions, is capable of isomerising glucose to levulose, a cellulose ester surrounding said cells, and a filler which comprises sparingly water-soluble compounds selected from the group consisting of (1) at least one sparingly water soluble magnesium compound and (2) a mixture of at least one sparingly water soluble magnesium compound and at least one sparingly water-soluble cobalt compound wherein said sparingly soluble magnesium compound is present in the filler in an amount of from 50 to about 100% by weight, based on the weight of the filler, said sparingly soluble cobalt compound is present in said filler in an amount of from about 50 to about 0% by weight, based on the weight of the filler, and said filler is present in said composition in an amount of from about 5 to about 100% by weight, based on the dry weight of said cells.

2. A composition according to claim 1, in which the cellulose ester is selected from at least one member of the group consisting of cellulose diacetate and a mixture of cellulose diacetate and cellulose triacetate.

3. A composition according to claim 1 in which the cells are of at least one micro-organism selected from at least one member of the group consisting of *Aerobacter cloacae*; and Arthrobacter; *Bacillus coagulans*; *Lactobacillus brevis*; *Streptomyces phaeochromogenes, echinatus, flavovirens, achromogenes, albus, olivaceus, olivochromogenes, violaceoniger, bikiniensis* and *venezuelae* and *Actinoplanes missouriensis*.

4. A composition according to claim 1 in which the sparingly water-soluble magnesium compound is selected from at least one member of the group consisting of magnesium oxide, magnesium phosphate and basic magnesium carbonate and a mixture thereof.

5. A composition according to claim 1 in which the filler contains both a sparingly water-soluble magnesium compound and a sparingly water-soluble cobalt compound.

6. A composition according to claim 5 in which the sparingly water-soluble cobalt compound is selected from at least one member of the group consisting of cobalt II hydroxide, cobalt II carbonate, cobalt II orthophosphate and cobalt II oxalate.

7. A composition according to claim 1 in which the filler is a cation exchange resin carrying sulphonic groups, which has been saturated with ions selected from the group consisting of $Mg^{++}$ ions and a mixture of $Mg^{++}$ ions and $Co^{++}$ ions, dried and ground.

8. A composition according to any one of claims 1 to 7 which contains 25 to 100% of a cellulose ester, calculated as the weight of dry material based on the weight of the dry cells, and 5 to 100% of filler, calculated as the weight of dry material based on the weight of the dry cells.

9. A composition according to claim 8 which contains about 50% by weight of a cellulose ester and about 50% by weight of filler, the percentages being calculated as the weight of dry material based on the weight of the dry cells.

10. A process for preparing an enzymatic composition which comprises
    (a) providing a slurry of micro-organism cells having glucose-isomerase immobilized therein or capable of being immobilized therein,
    (b) drying the slurry to a dry material content of 20 to 95% by weight, .
    (c) mixing the dried slurry with 5 to 100% by weight, based on the weight of the dry cells, of a filler comprising 50 to 100% by weight of a sparingly water-soluble magnesium compound and 50 to 0% by weight of a sparingly water-soluble cobalt compound,
    (d) adding a cellulose ester in an amount of 25 to 100% by weight, based on the weight of the dry cells, in the form of a 5 to 200% w/v sol in a water-miscible solvent, with the proviso that the order of steps (c) and (d) are (d) following (c), or (c) following (d), (e) adding an amount of solvent which is 1 to 10 times the weight of the dry cells, and water such that the final mixture contains water in an amount 0.6 to 8 times the weight of the cellulose ester and the final weight ratio of water to solvent is less than 0.2:1, (f) shaping the mixture obtained, and (g) drying the shaped mixture at 15° to 30° C., and (h) immobilizing the glucose isomerase within said micro-organism cells when this has not been satisfactorily achieved in step (a) by treatment of said micro-organism cells with glutaraldehyde, either when the have been produced, or in the slurry of the cells and a cellulose ester before adding the filler in which case the order of steps (c) and (d) are reversed, or in the shaped composition which has been dried.

11. A process according to claim 10 wherein steps (b) through (e) respectively comprise (b) drying the slurry to a dry material content of about 30% by weight, (c) mixing the dried slurry with about 50% by weight, based on the weight of the dry cells, of a filler comprising about 50% by weight of a sparingly soluble magnesium compound and 50 to 0% by weight of a sparingly soluble cobalt compound, (d) adding a cellulose ester in an amount of about 50% by weight based on the weight of dry cells, in the form of about 10% w/v sol in an acetone, and (e) adding an amount of solvent which is 1 to 10 times the weight of the dry cells, and water such that the final mixture contains water in an amount of about 3 times the weight of the cellulose ester and the final weight ratio of water to acetone is less than 0.2:1.

12. A process according to any one of claims 10 or 11, in which the composition is shaped by spreading a 1 to 3 mm thick layer of the composition over a substrate, partially drying the composition, cutting up the composition into small plates and further drying these plates.

13. A process according to any one of claims 10 or 11 in which the composition is shaped by extruding the composition into filaments, coagulating the surface of the extruded filaments with hot air or by immersion in water, and then optionally drying the filaments.

14. A process for isomerising glucose to levulose, which comprises passing an aqueous glucose syrup of pH 8 to 9, which has a glucose concentration not exceeding 60%, by weight, based on the weight of the syrup, and to which no magnesium ions have been added, at 50° to 75° C. through a bed comprising an enzymatic composition as claimed in claim 1.

15. A process for isomerising glucose to levulose, which comprises passing an aqueous glucose syrup of pH 8 to 9, which has a glucose concentration not exceeding 60%, by weight, based on the weight of the syrup, and to which magnesium ions have been added to give a content of 2 to 10 mg magnesium liter at 50° to 75° C. through a bed comprising an enzymatic composition as claimed in claim 1.

16. A process according to claim 14 or 15 in which the glucose syrup is of pH about 8.5 and has a glucose concentration of about 45% by weight, based on the weight of the syrup, and the temperature at which the syrup is passed through the bed is about 60° C.

* * * * *

UNITED STATES PATENT AND TRADEMARK OFFICE
CERTIFICATE OF CORRECTION

PATENT NO. : 4,264,732
DATED : April 28, 1981
INVENTOR(S) : Guy Lartigau et al

It is certified that error appears in the above-identified patent and that said Letters Patent are hereby corrected as shown below:

Column 9, line 55, correct "glycose" to read -- glucose --.

Signed and Sealed this

Thirteenth Day of July 1982

[SEAL]

Attest:

GERALD J. MOSSINGHOFF

*Attesting Officer*   *Commissioner of Patents and Trademarks*